United States Patent
Leech et al.

(10) Patent No.: US 9,452,237 B2
(45) Date of Patent: Sep. 27, 2016

(54) SMART, SELF-DECONTAMINATING POLYMER AND METHOD FOR INHIBITING THE GROWTH OF A BACTERIA AND FUNGUS

(71) Applicant: Agentase, LLC, Pittsburgh, PA (US)

(72) Inventors: Anna M. Leech, Pittsburgh, PA (US); Jeremy P. Walker, Oakmont, PA (US); Scott Donahue, Allison Park, PA (US); Jermaine D. Johnson, Pittsburgh, PA (US); Jessica J. Sinclair, Murrysville, PA (US)

(73) Assignee: FLIR Detection, Inc., Stillwater, OK (US)

( * ) Notice: Subject to any disclaimer, the term of this patent is extended or adjusted under 35 U.S.C. 154(b) by 0 days.

(21) Appl. No.: 13/915,839

(22) Filed: Jun. 12, 2013

(65) Prior Publication Data
US 2013/0344130 A1 Dec. 26, 2013

Related U.S. Application Data

(60) Provisional application No. 61/660,065, filed on Jun. 15, 2012.

(51) Int. Cl.

| | |
|---|---|
| A61L 15/38 | (2006.01) |
| A61K 38/44 | (2006.01) |
| A61F 13/00 | (2006.01) |
| A61L 15/26 | (2006.01) |
| A61L 15/46 | (2006.01) |
| A61L 15/42 | (2006.01) |
| A61L 15/44 | (2006.01) |
| A61K 9/70 | (2006.01) |
| A61K 9/06 | (2006.01) |

(52) U.S. Cl.
CPC .......... *A61L 15/38* (2013.01); *A61F 13/00059* (2013.01); *A61F 13/00063* (2013.01); *A61K 38/443* (2013.01); *A61L 15/26* (2013.01); *A61L 15/425* (2013.01); *A61L 15/44* (2013.01); *A61L 15/46* (2013.01); *A61K 9/06* (2013.01); *A61K 9/7007* (2013.01); *A61L 2300/404* (2013.01); *A61L 2300/434* (2013.01); *A61L 2420/06* (2013.01)

(58) Field of Classification Search
None
See application file for complete search history.

(56) References Cited

U.S. PATENT DOCUMENTS

| | | | |
|---|---|---|---|
| 4,576,817 A | 3/1986 | Montgomery et al. | |
| 5,610,025 A | 3/1997 | White et al. | |
| 5,885,412 A * | 3/1999 | Paart et al. | 162/5 |
| 6,228,128 B1 | 5/2001 | Johansen et al. | |
| 6,759,220 B1 | 7/2004 | LeJeune et al. | |
| 7,713,955 B2 | 5/2010 | Whiteford et al. | |
| 7,731,954 B2 | 6/2010 | Davis et al. | |
| 7,927,588 B2 | 4/2011 | Davis et al. | |
| 2006/0034816 A1 | 2/2006 | Davis et al. | |
| 2006/0127461 A1 * | 6/2006 | Bloor | 424/445 |
| 2007/0190122 A1 | 8/2007 | Davis et al. | |
| 2010/0135926 A1 | 6/2010 | Barrett et al. | |

FOREIGN PATENT DOCUMENTS

| | | |
|---|---|---|
| WO | 9702811 | 1/1997 |
| WO | 9805362 | 2/1998 |
| WO | 2007134180 A2 | 11/2007 |
| WO | 2008041218 A1 | 4/2008 |

OTHER PUBLICATIONS

Arica et al. (J Chem Tech Biotechnol 1993, 58, 287-292).*
Wan, A. T. et al., Determination of Silver in Blood, Urine, and Tissues of Volunteers and Burn Patients, Clin. Chem., 1991, 1683-1687, vol. 37, No. 10.
Lansdown, A. B. G. et al., A Pharmacological and Toxicological Profile of Silver as an Antimicrobial Agent in Medical Devices, Advances in Pharmacological Sciences, 2010, 1-16, vol. 2010, Hindawi Publishing Corporation.
Lowbury, E. J. L. et al., Topical Chemoprophylaxis with Silver Sulphadiazine and Silver Nitrate Chlorhexidine Creams: Emergence of Sulphonamide-Resistant Gram-Negative Bacilli, British Medical Journal, 1976, 493-496, vol. 1.
Iguchi, T. et al., Commonality in Signaling of Endocrine Disruption From Snail to Human, BioScience, 2008, 1061-1067, vol. 58, No. 11.
International Maritime Organization, Anti-Fouling Systems, 2002, 1-31.
International Search Report and Written Opinion for PCT/US2013/45331 filed Jan. 14, 2014.
Extended European Search Report for EP 13804843.4 dated Dec. 15, 2017.

* cited by examiner

*Primary Examiner* — Patricia Duffy
*Assistant Examiner* — Garen Gotfredson
(74) *Attorney, Agent, or Firm* — Buchanan Ingersoll & Rooney PC; Craig G. Cochenour (57) ABSTRACT

A smart antimicrobial material and dressing to inhibit microbial growth is provided. Endogenous chemicals, such as metabolites produced from bacteria are utilized as chemical substrates and converted by enzymes to produce a disinfecting compound that will in turn inhibit the targeted microorganism. The material shall remain passive until such time as it encounters a microbe which expresses and/or secretes specific metabolites or markers. The enzyme or enzymes embedded in the smart material converts the metabolite into a disinfecting compound, which in turn either kills the microorganism or prevents it from multiplying on the surface of the material.

19 Claims, 3 Drawing Sheets

SMART, SELF-DECONTAMINATING POLYMER AND METHOD FOR INHIBITING THE GROWTH OF A BACTERIA AND FUNGUS

CROSS-REFERENCE TO RELATED APPLICATION

This utility patent application claims the benefit of pending U.S. Provision Patent Application Ser. No. 61/660,065, filed on Jun. 15, 2012. The entire contents of U.S. Provisional Patent Application Ser. No. 61/660,065 is incorporated by reference into this utility patent application as if fully written herein.

BACKGROUND OF THE INVENTION

1. Field of the Invention

The present invention relates to the production of a smart antimicrobial system to inhibit microbial growth. Endogenous chemicals, such as metabolites produced from bacteria are utilized as chemical substrates and then converted by enzymes to produce disinfecting compounds that in turn inhibit the targeted microorganism.

2. Description of the Background Art

Biocides and more specifically, antimicrobials are commonly used in medicine and agriculture to control the population of undesired organisms. Most biocides are not specific in killing a particular type or class of organism and have negative effects on other (non-target) cells and tissues and can be harmful to the environment.

Furthermore, the use of silver containing products for wound treatment involves the risk of both argyria, or silver toxicity (Abraham T. Wan et. al., *Determination of Silver in Blood, Urine, and Tissues of Volunteers and Burn Patients*, 37 Clin. Chem. 1683, (1991); Alan B. G. Lansdown, *A Pharmacological and Toxiological Profile of Silver as an Antimicrobial Agent in Medical Devices*, 2010 Advances in Pharmacological Sciences, (2010).) and the emergence of resistant organisms (E J L Lowbury et. al., *Topical chemoprophylaxis with silver sulphadiazine and silver nitrate chlorhexidine creams: emergence of sulphonamide-resistant Gram-negative bacilli*, 1 British Medical Journal 493, (1976)). Tributyltin, widely used in anti-fouling treatments for maritime vessels since the 1960's, has been shown to persist in the environment and have adverse effects across many species (Taisen Iguchi & Yoshinao Katsu, *Commonality in Signaling of Endocrine Disruption from Snail to Human*, 58 BioScience 1061, (2008); International Maritime Organization, *Anti-fouling systems* (2002)). This necessitates diligence in deploying such non-specific biocides, as their use should be avoided when the targeted biologicals are not present at problematic concentrations.

However, biocides must be readily available as soon as conditions change and the hazard has exceeded a 'threat' concentration. The object of this invention is to define a protein polymer material that generates biocides and antimicrobials only when conditions dictate that disinfection is necessary. Appropriate 'triggering' environmental conditions include, but are not limited to, signs of physical activity such as increases in body temperature and perspiration, signs of microbial contamination including volatile and non-volatile organics produced as metabolic products from propagating organisms (including excreted proteases, organic acids, and biogenic amines) as well as conditions in the environment that may foster microbial growth including excess humidity, bodily fluids and waste materials, and the presence of exopolysaccharide. There are no materials currently which specifically produce antimicrobial compounds, such as oxidizers, only when the target organism is present. Most of the materials currently available either require activation prior to use or are active immediately out of the package.

Hydrogen peroxide, an oxidizer, has been used for many years to disinfect wounds. One problem is that its rapid breakdown into water and oxygen make it difficult to use for prolong periods of time. Also very high concentrations (>3%) of hydrogen peroxide are toxic to the host cells. That is why it is important for an on demand source of an oxidizer, such as hydrogen peroxide, to disinfect wounds only when 'triggering' conditions are present.

U.S. Pat. No. 6,228,128 Johansen discloses treatment of microorganisms and/or viruses comprising treating said microorganisms and/or viruses with an effective amount of fungal lactase enzymes and an effective amount of one or more enhancers in the presence of oxygen. The enzyme here requires enhancers for the invention to work effectively and the enzymes are always active after activation.

U.S. Pat. No. 7,927,588 Davis et al. discloses a dressing containing an enzyme and a dressing containing a water source for the dressing to be activated. It was not suggested that the enzyme could be turned on by 'triggering' conditions.

U.S. Pat. No. 7,731,954 Davis et al. discloses a skin dressing comprising oxidoreductase enzyme wherein the enzyme is present in a hydrated condition. The enzymes are hydrated prior to use and are always active. U.S. Pat. No. 7,731,954 can only last for up to 2 days after activation. The invention does not respond to environmental conditions and the ingress of catalase is an efficiency reducing condition. It does not proscribe a way to inhibit catalase from using the hydrogen peroxide that is produced from the oxidoreductase enzyme nor a way of being active longer than 2 days after application.

U.S. Pat. No. 7,713,955 Whiteford et al. describes antimicrobial coatings for a surface. It discloses using a bridged polycyclic compound based coating system to impart self-cleaning properties to a surface. It does not disclose using enzymes that are can be activated by the environment that produce oxidizers when a target organism is present.

U.S. Pat. No. 6,759,220 LeJeune et al. discloses the loading of an enzyme into a polymer and how to improve the loading. It does not disclose having the enzymes only activated by the environment. It further does not teach that the polymers could be for anti-microbial purposes nor as a dressing.

It is desirable to make a material which generates antimicrobial compounds when a target organism is present, the material does not need a substrate to work and can be employed for long periods of time, such for example but not limited to, a time period of greater than three to four weeks.

SUMMARY OF THE INVENTION

This invention relates to a smart antimicrobial system to inhibit microbial growth. Endogenous chemicals, such as metabolites produced from bacteria will be utilized as chemical substrates and converted by enzymes to produce disinfecting compounds that will in turn inhibit the targeted microorganism. The material shall remain passive until such time as it encounters a microbe which expresses and/or secretes specific metabolites or markers. The enzyme or enzymes embedded in the smart material converts the metabolite into a disinfecting compound, which in turn either kills the microorganism or prevents it from multiplying on the surface of the material. Such materials have potential utility for food packaging, hospital coatings, architectural coatings, wound healing materials and prosthetic liners, coatings for the interiors of cars, airplanes and other transportation devices, as well as coatings for mobile personal electronic devices such as cell phones, laptop computers, portable media devices, and other personal items.

In an embodiment of this invention, a material comprising an excipient, a first polymer mixed with the excipient, at least one enzyme contained within the first polymer, and an aqueous composition, wherein the enzyme is in a sufficient amount to catalyze a conversion of a chemical constituent placed in contact with the material, and wherein the enzyme is capable of being activated in the presence of a target analyte to release at least one or more of a disinfectant, an antimicrobial, an antioxidant, or combinations thereof from the first polymer. Preferably, this material includes wherein the enzyme is immobilized within the first polymer or entrapped within the first polymer. Another embodiment of this material includes wherein the material has at least one initiator composition for photopolymerizing the material to form a gel or film. Another embodiment of this invention includes at least one inhibitor of catalase activity, such as for example but not limited to hydroxylamine, silver, oxytetracycline, azide, and dithiothreitol, and combinations thereof.

In another embodiment of this invention, a material is provided comprising an excipient, a first polymer mixed with the excipient, at least one protein that is covalently linked or crosslinked to the first polymer, and an aqueous composition, wherein the protein is in a sufficient amount to catalyze a conversion of a chemical constituent placed in contact with the material, and wherein the protein is capable of undergoing hydrolysis in response to a target analyte to release at least one or more of a disinfectant, an antimicrobial, an antioxidant, or combinations thereof from the first polymer. Another embodiment of this invention includes this material including at least one biocide composition that, preferably, is physically entrapped within the first polymer or covalently tethered to the first polymer. Another embodiment of this invention includes this material including at least one biocide composition, wherein the biocide composition is physically tethered to the protein or in contact with the crosslinked polymer such that the biocide is released from the crosslinked polymer upon cleavage of the protein from the first polymer.

Another embodiment of this invention provides a dressing comprising a single layer comprising a first side and a second side, wherein the first side is facing an opposite direction relative to the second side, and wherein the first side and the second side are disposed in juxtaposition to each other forming the layer having a desired height, length and width, a first polymer disposed on at least the first side of the layer or within the layer, and optionally including wherein the first polymer is disposed on the second side of the layer or within the layer, at least one enzyme contained within the first polymer, and an aqueous composition contained within the single layer, wherein the enzyme is in a sufficient amount to catalyze a conversion of a chemical constituent placed in contact with the layer, and wherein the enzyme is capable of being activated in the presence of a target analyte to release at least one or more of a disinfectant, an antimicrobial, an antioxidant, or combinations thereof from the first polymer. Preferably, this dressing includes wherein the enzyme is immobilized within the first polymer or wherein the enzyme is entrapped within the first polymer. Another embodiment of this dressing comprises wherein the single layer, as described herein, further comprises at least one inhibitor of catalase activity that is disposed on at least the first side of the layer or within the layer, and optionally including wherein the inhibitor of catalase activity is disposed on the second side of the layer or within the layer.

In a preferred embodiment of this invention, the dressing, as described herein, comprises a cover attached to at least a portion of either the first side of the layer or the second side of the layer for adhering the layer to a wound site of a patient or for adhering the layer to an area proximate to the wound site of the patient. More preferably, the dressing of this invention includes wherein the layer is biodegradable.

Another embodiment of this invention provides a dressing comprising a single layer comprising a first side and a second side, wherein the first side is facing an opposite direction relative to the second side, and wherein the first side and the second side are disposed in juxtaposition to each other forming the layer having a desired height, length and width, a first polymer disposed on at least the first side of the layer or within the layer, and optionally including wherein the first polymer is disposed on the second side of the layer or within the layer; at least one protein that is covalently linked or crosslinked to the first polymer, and wherein the protein is disposed on at least the first side of the layer or within the layer, and optionally including wherein the protein is disposed on the second side of the layer or within the layer, and an aqueous composition disposed within the layer, wherein the protein is in a sufficient amount to catalyze a conversion of a chemical constituent placed in contact with the layer, and wherein the protein is capable of undergoing hydrolysis in response to a target analyte to release at least one or more of a disinfectant, an antimicrobial, an antioxidant, or combinations thereof from the first polymer. Preferably, this dressing includes at least one biocide composition. Preferably, the biocide composition is physically entrapped within the first polymer or covalently tethered to the first polymer. In another embodiment of this invention, the dressing includes at least one biocide composition, wherein the biocide composition is physically tethered to the protein or in contact with the crosslinked polymer such that the biocide is released from the crosslinked polymer upon cleavage of the protein from the first polymer. In another embodiment of the dressing of this invention, as described herein, a cover is attached to at least a portion of either of the first side of the layer or the second side of the layer for adhering the material to a wound site of a patient or for adhering the material to an area proximate to a wound site of a patient. In another embodiment of the dressing of this invention, it is preferable that the layer of the dressing is biodegradable.

In yet another embodiment of this invention, a method of providing therapy to the dermis or epidermis of a patient is provided comprising placing a dressing in contact with a patient's epidermis or dermis, the dressing comprising (i) a single layer comprising a first side and a second side, wherein the first side is facing an opposite direction relative to the second side, and wherein the first side and the second side are disposed in juxtaposition to each other forming the layer having a desired height, length and width, (ii) a first polymer disposed on at least the first side of the layer or within the layer, and optionally including wherein the first polymer is disposed on the second side of the layer or within the layer, (iii) at least one enzyme contained within the first polymer, and (iv) an aqueous composition contained within the layer, wherein the enzyme is in a sufficient amount to catalyze a conversion of a chemical constituent placed in contact with the layer, and wherein the enzyme is capable of being activated in the presence of a target analyte to release at least one or more of a disinfectant, an antimicrobial, an antioxidant, or combinations thereof from the first polymer; contacting at least one target analyte with the said dressing, and preferably the layer of the dressing, for forming at least one product selected from the group of a disinfectant, an antimicrobial, an antioxidant, or combinations thereof; and releasing the product to the patient's epidermis or dermis for providing therapy to the patient. In another embodiment of this invention, this method further provides including at least one initiator composition for photopolymerizing the layer to form a gel or film. In another embodiment of this invention, this method further provides including at least one inhibitor of catalase activity that is disposed on at least the first side of the layer or within the layer, and optionally including wherein the inhibitor of catalase activity is disposed on the second side of the layer or within the layer.

Another embodiment of this invention provides a method of providing therapy to the dermis or epidermis of a patient comprising placing a dressing in contact with a patient's epidermis or dermis, the dressing comprising (i) a single layer comprising a first side and a second side, wherein the first side is facing an opposite direction relative to the second side, and wherein the first side and the second side are disposed in juxtaposition to each other forming the layer having a desired height, length and width, (ii) a first polymer disposed on at least the first side of the layer or within the layer, and optionally including wherein the first polymer is disposed on the second side of the layer or within the layer, (iii) at least one protein that is covalently linked or crosslinked to the first polymer, and (iv) an aqueous composition that is disposed within the layer, wherein the protein is in a sufficient amount to catalyze a conversion of a chemical constituent placed in contact with the layer, and wherein at least one protein is capable of undergoing hydrolysis in response to a target analyte to release at least one or more of a disinfectant, an antimicrobial, an antioxidant, or combinations thereof from the first polymer; contacting at least one target analyte with the dressing, or preferably the layer of the dressing, for forming at least one product selected from the group of a disinfectant, an antimicrobial, an antioxidant, or combinations thereof; and releasing the product to the patient's epidermis or dermis for providing therapy to the patient. In another embodiment of this invention, this method includes providing an initiator composition for photopolymerizing the layer to form a gel or film. In another embodiment of this invention, this method includes providing at least one inhibitor of catalase activity that is disposed on at least the first side of the layer or within the layer, and optionally including wherein the inhibitor of catalase is disposed on the second side of the layer or within the layer. In another embodiment of this invention, this method includes providing at least one biocide composition. Preferably, the biocide composition is physically tethered to the protein or in contact with the crosslinked polymer such that the biocide is released from the crosslinked polymer upon cleavage of the protein from the first polymer.

Another embodiment of this invention provides a method for inhibiting the growth of a bacteria and/or fungus comprising applying to a surface that is suspect of contamination with bacteria and/or fungus, an effective amount of a material comprising (i) an excipient, (ii) a first polymer mixed with the excipient, (iii) at least one enzyme contained within the first polymer, and (iv) an aqueous composition, wherein the enzyme is in a sufficient amount to catalyze a conversion of a chemical constituent placed in contact with the material, and wherein the enzyme is capable of being activated in the presence of a target analyte to release at least one or more of a disinfectant, an antimicrobial, an antioxidant, or combinations thereof from the first polymer; providing at least one target analyte from the suspect contaminated surface to contact the enzyme for forming at least one product selected from the group consisting of a disinfectant, an antimicrobial, an antioxidant, or combinations thereof; and releasing the product to the surface for inhibiting the bacteria and/or the fungus. In another embodiment of this invention, this method includes providing at least one initiator composition for photopolymerizing the material to form a gel or film. In another embodiment of this invention, this method includes applying at least one inhibitor of catalase activity to the surface.

Another embodiment of this invention provides a method for inhibiting the growth of a bacteria and/or fungus comprising applying to a surface that is suspect of contamination with bacteria and/or fungus, an effective amount of a material comprising (i) an excipient, (ii) a first polymer mixed with the excipient, (iii) at least one protein that is covalently linked or crosslinked to the first polymer, and (iv) an aqueous composition, wherein the protein is in a sufficient amount to catalyze a conversion of a chemical constituent placed in contact with the material, and wherein the protein is capable of undergoing hydrolysis in response to a target analyte to release at least one or more of a disinfectant, an antimicrobial, an antioxidant, or combinations thereof from the first polymer; providing at least one target analyte from the suspect contaminated surface to contact the protein for forming at least one product selected from the group consisting of a disinfectant, an antimicrobial, an antioxidant, or combinations thereof; and releasing the product to the surface for inhibiting the bacteria and/or the fungus. In another embodiment of this invention, this method includes providing at least one initiator composition for photopolymerizing the material to form a gel or film. In another embodiment of this invention, this method includes applying at least one inhibitor of catalase activity to the surface. In another embodiment of this invention, this method includes providing at least one biocide composition. Preferably, the biocide composition is physically tethered to the protein or in contact with the crosslinked polymer such that the biocide composition is released from the crosslinked polymer upon cleavage of the protein from the first polymer.

DETAILED DESCRIPTION OF THE INVENTION

As used herein, the term "chemical constituents" is any chemical that can be trapped inside or bound to a polymer such as dyes, buffers and anti-microbials. As used herein, the term "material" is a polymer, hydrogel, fabric or film. As used herein, the term "disinfecting compound" is any compound selected from the group of disinfectants, antiseptics, antimicrobials, biocides or a combination thereof.

The present invention provides a smart antimicrobial material and dressing to inhibit microbial growth. Endogenous chemicals, such as metabolites produced from bacteria will be utilized as chemical substrates and converted by enzymes to produce disinfecting compounds that will in turn inhibit the targeted microorganism. The material shall remain passive until such time as it encounters a microbe which expresses and/or secretes specific metabolites or markers. The enzyme or enzymes embedded in the smart material converts the metabolite into a disinfecting compound, which in turn either kills the microorganism or prevents it from multiplying on the surface of the material. Such materials have potential utility for food packaging, hospital coatings, architectural coatings, wound healing materials and prosthetic liners, coatings for the interiors of cars, airplanes and other transportation devices, as well as coatings for mobile personal electronic devices such as cell phones, laptop computers, portable media devices, and other personal items.

Figure 3:
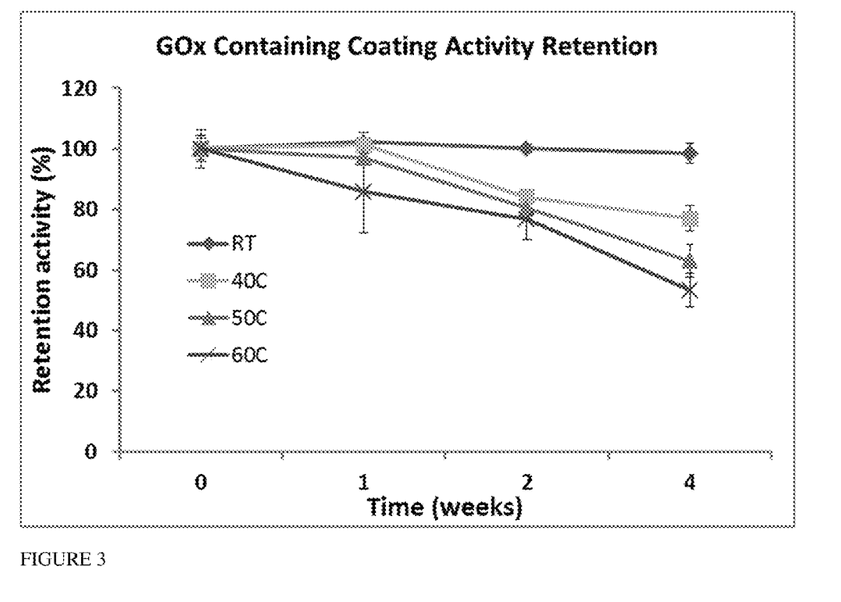
FIG. 3 shows the enzyme activity retention of the polymer over time after storage at various temperatures.

Accordingly, the present invention provides a smart polymer which can supply on demand one or more disinfecting compounds. The production of such disinfecting compounds will only be turned on in the presence of target analytes which are found in the environment. The present invention can remain active for extended periods of time, such as for example for at least 4 weeks (See FIG. 3). The smart polymer comprises chemical constituents and enzymes that generate disinfecting compounds on demand. The demand may be evidenced for example, but not limited to, by signs of physical activity such as increases in body temperature and perspiration, through signs of microbial contamination as metabolic products such as volatile and non-volatile organics (including but not limited to, organic acids, biogenic amines and excreted proteases) are produced, as well as through changes in environmental conditions which may foster microbial growth including excess humidity, bodily fluids and waste materials, and the presence of exopolysaccharide. These materials have broad based applicability such as, but not limited to, in the fields of acute and chronic wound care, minimization of stress-based wear effects on skin tissue, improving skin interactions with a host of materials (such as but not limited to prosthesis and footwear), pharmacology, as well as smart anti-fungal and anti-microbial surfaces and coatings, among others.

As used herein, the term "patient" includes members of the animal kingdom, including animals, *Homo sapiens*, and warm or cold blooded creatures. As used herein the term "wound" includes an injury to a part or tissue or organ of a patient's body, or an incision to a part or tissue or organ of a patient's body. A wound may be caused by, for example but not limited to, physical trauma and may be characterized by tearing, cutting, piercing or breaking of the patient's body part, tissue or organ.

As used herein, the term "effective amount" is that amount required to bring about a desired result, such as for example, the amount of a material or composition required to inhibit the growth of a bacteria or fungus.

As used herein, the term "crosslinking" includes the attachment of two chains of polymer molecules by bridges composed of either an element, or group, or a compound which join certain carbon atoms of the chains by primary chemical bonds. The bridges are referred to as the crosslinking agents. As understood by those persons skilled in the art, crosslinking occurs in nature in substances made up of polypeptide chains which are joined by disulfide bonds of a cystine residue, such as for example in keratins, insulin and other proteins. For example, those persons skilled in the art understand that polysaccharide molecules may crosslink to form stable gel structures. Crosslinking may be effected artificially such as for example by addition of a chemical substance (cross-linking agent) and exposing the mixture to heat or by subjecting the polymer to high-energy radiation. For example, those persons skilled in the art understand that crosslinking of polyethylene may be carried out by means of high-energy radiation or with an organic peroxide.

Figure 4:
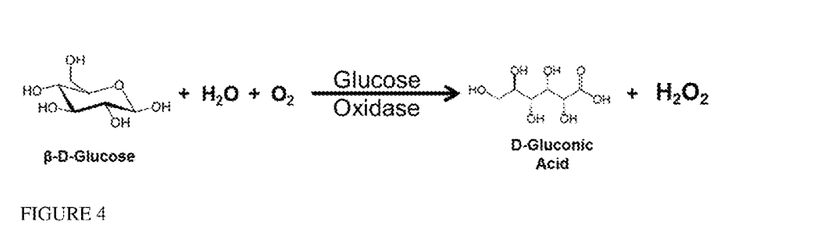
FIG. 4 shows the conversion of β-D-Glucose, water and oxygen to D-Gluconic acid and hydrogen peroxide in the presence of Glucose Oxidase (an enzyme).
Figure 5:
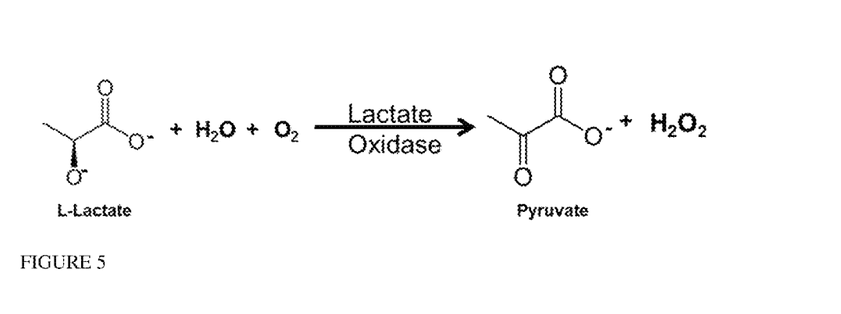
FIG. 5 shows the conversion of L-Lactate, water and oxygen to pyruvate and hydrogen peroxide in the presence of Lactate Oxidase (an enzyme).

One embodiment of the invention entails the covalent immobilization or physical entrapment of oxidase enzymes within polymer fabrics for use on the skin. Perspiration carries many constituents (lactate, glucose, creatine, etc) that are substrates (reactants) for oxidase enzymes (see FIGS. 4 and 5). Active and stable oxidases in the fabric respond by generating hydrogen peroxide, which has utility as a disinfectant. In a more preferred embodiment, the polymer also carries a haloperoxidase (i.e. chloroperoxidase, Bromoperoxidase, Iodoperoxidase), an enzyme that generates halogens in the presence of halide salts and hydrogen peroxide. This material, when exposed to perspiration generates low levels of chlorine and other strong oxidants (such as reactive oxygen species) and kills biologicals that might otherwise propagate in the perspiration fluid. The material, in the absence of perspiration, is otherwise benign and has no tangible impact on the skin.

Another embodiment of the invention utilizes oxidase enzymes that react with metabolic products of propagating bacteria within wounds including, but not limited to, organic acids and biogenic amines. As the concentration of propagating bacteria within the wound increases, the concentrations of metabolic products also increase in the wound fluid. A wound dressing comprised of the subject biocomposite polymer carrying mixed oxidases generates hydrogen peroxide as colony counts within a wound increase. Again, a preferred embodiment of this invention carries also carries haloperoxidase to generate halogens in the presence of halide salts and hydrogen peroxide. This smart dressing has no chemical activity or impact on the wound until the metabolic products within the wound fluid deliver sufficient metabolic products to the dressing to trigger the synthesis of disinfectants.

Further, an additional embodiment of the invention utilizes a biocomposite crosslinked polymer coating that is comprised of a structural protein and a synthetic monomer. Entrained or physically entrapped within the polymer is a biocide. Many microorganisms, molds, and fungi release proteases as they propagate and grow. When such organisms propagate on the surface of the described biopolymer material, excreted proteases cleave peptide bonds in the structural proteins within the polymer, changing the morphology of the polymer and effectively increasing the distance between crosslinks within the matrix. The larger distance between crosslinks improves diffusion and release of entrained biocides. In summary, the coating remains intact and stable until a propagating microorganism triggers the release of a biocide through the excretion of certain proteases.

Another embodiment of this invention provides a material comprising an excipient; a first polymer mixed with the excipient; at least one enzyme contained within the first polymer; and an aqueous composition, wherein the enzyme is in a sufficient amount to catalyze a conversion of a chemical constituent placed in contact with the material, and wherein the enzyme is capable of being activated in the presence of a target analyte to release at least one or more of a disinfectant, an antimicrobial, an antioxidant, or combinations thereof from the first polymer. Preferably, the antimicrobial includes peroxides and halogen gases. The aqueous composition may be for example, but not limited to, water or a buffer. Preferably the aqueous composition is from 0.1 weight percent (0.1 wt. %) to 99.0 weight percent (99.0 wt. %) of the total weight of the material, and more preferably from 5.0 wt. % to 75.0 wt. % of the total weight of the material. Another embodiment of this material, as described herein, includes wherein the excipient is a second polymer that is different than the first polymer. Preferably, the material of the present invention, as described herein, includes wherein the enzyme is covalently attached to the first polymer or wherein the enzyme is immobilized or entrapped within the first polymer. The enzyme is at least one selected from the group consisting of an oxidoreductase, a transferase, a hydrolase, a lyase, an isomerase, and a ligase. More preferably, the enzyme is at least one selected from the group consisting of an oxidase, a protease, a lipase, a peroxidase, a tyrosinase, a glycosidase, a nuclease, an aldolase, a phosphatase, a sulfatase, and a dehydrogenase. More preferably, the enzyme is an oxidase that is a glucose oxidase or a lactate oxidase. More preferably the enzyme is a peroxidase that is a haloperoxidase. Most preferably, the haloperoxidase is a chloroperoxidase. Most preferably, the material of the present invention, as described herein, includes wherein the enzyme is one or more oxidase enzymes that is activated by one or more of a target analyte that is a metabolic byproduct of one or more of the chemical constituent that is a propagating microorganism wherein the metabolic byproduct is converted into the disinfectant that is a hydrogen peroxide. The metabolic byproducts of the propagating microorganism are preferably selected from the group consisting of biogenic amines and organic acids.

The first polymer of the present invention may be any number of polymers. The polymers may be for example cationic, anionic, or nonionic polymers. For example, the polymers may be amino methylated poly(acrylamide), quaternized derivatives of N,N-dimethylaminoethylmethacrylate, acrylamide, polyacrylamide, acrylic acid, polyacrylic acid, methacrylic acid, and polysulfostyrene, Preferably, the first polymer is a polyurethane polymer or a polyethylene glycol diacrylate polymer.

The excipient of the present invention may be an active or an inactive composition. Those skilled in the art understand that an active excipient imparts not only a physical characteristic to a formulation such as for example a base (or vehicle) to which components of a formulation are added or dispersed within, but also imparts its own therapeutic properties, such as for example, petrolatum, glycerin (glycerol), and dimethicone, all of which have emollient properties. In another embodiment of this invention, for example, the excipient may be a polymer or copolymer, such polymer and copolymers are described herein. When the excipient is a polymer, the excipient is referred to herein as the "second polymer" to distinguish it from the "first polymer" of this invention. The second polymer may be the same or different than the first polymer of the material. More preferably, the excipient of the present invention is polyethylene glycol.

Another embodiment of the material of the present invention, as described herein, includes at least one initiator composition. Preferably, the initiator composition is an ultraviolet initiator composition. Preferably, the material of the present invention is photopolymerized to form a gel or film.

In another embodiment of the present invention, as described herein, the material further includes at least one inhibitor of catalase activity. Preferably this inhibitor of catalase activity is at least one selected from the group consisting of hydroxylamine, silver, oxy-tetracycline, azide, and dithiothreitol. More preferably, this inhibitor of catalase activity is covalently bonded to the first polymer of the material.

Another embodiment of this invention provides a material comprising an excipient; a first polymer mixed with the excipient; at least one protein that is covalently linked or crosslinked to the first polymer; and an aqueous composition, wherein the protein is in a sufficient amount to catalyze a conversion of a chemical constituent placed in contact with the material, and wherein the protein is capable of undergoing hydrolysis in response to a target analyte to release at least one or more of a disinfectant, an antimicrobial, an antioxidant, or combinations thereof from the first polymer. Preferably, this material further includes at least one biocide composition, wherein the biocide composition is physically entrapped within the first polymer or covalently tethered to the first polymer. More preferably, the biocide composition is physically tethered to the protein or in contact with the crosslinked polymer such that the biocide is released from the crosslinked polymer upon cleavage of the protein from the first polymer.

Another embodiment of the present invention provides a dressing comprising a material having a single (one) layer comprising a first side and a second side, wherein the first side is facing an opposite direction relative to the second side, and wherein the first side and the second side are disposed in juxtaposition to each other forming the layer having a desired height, length and width; a first polymer disposed on or within at least the first side of the layer, and optionally including wherein the first polymer is disposed on or within the second side of the layer; at least one enzyme contained within the first polymer; and at least one aqueous composition contained within the material, wherein the enzyme is in a sufficient amount to catalyze a conversion of a chemical constituent placed in contact with the material, and wherein the enzyme is capable of being activated in the presence of a target analyte to release at least one or more of a disinfectant, an antimicrobial, an antioxidant, or combinations thereof from the first polymer. More preferably, the dressing, as described herein, includes wherein the antimicrobial includes peroxides and halogen gases. Most preferably, the dressing, as described herein, includes wherein the enzyme is one or more oxidase enzymes that is activated by one or more of a target analyte that is a metabolic byproduct of one or more of the chemical constituent that is a propagating microorganism wherein the metabolic byproduct is converted into the disinfectant that is a hydrogen peroxide. The dressing of the present invention, as described herein, includes wherein the metabolic by-products of the propagating microorganism are selected from the group consisting of biogenic amines and organic acids. For example, but not limited to, the metabolic byproducts of said propagating microorganisms are one or more selected from the group consisting of lactate, glucose, creatine, cadaverine, putrescine, histamine, and tyramine. It will be understood by those persons skilled in the art that when the enzyme of the dressing is a haloperoxidase that is immobilized within the first polymer, the haloperoxidase is capable of converting hydrogen peroxide into one or more of a halogen gas in the presence of one or more of a halide salt. In the dressing of this invention, as described herein the layer may be made of any number of compositions, such as for example, but not limited to, a film, a fiber, a fabric, a thread, a gauze, or a polymeric composition. The layer of the dressing must be able to physically support and allow for the first polymer, the enzyme, and the aqueous composition to be contained on or with in the layer. More preferably, the dressing, as described herein comprises wherein the enzyme is immobilized within the first polymer or wherein the enzyme is entrapped within the first polymer. The enzyme is at least one selected from the group consisting of an oxidoreductase, a transferase, a hydrolase, a lyase, an isomerase, and a ligase. Preferably, the enzyme is at least one selected from the group consisting of an oxidase, a protease, a lipase, a peroxidase, a tyrosinase, a glycosidase, a nuclease, an aldolase, a phosphatase, a sulfatase, and a dehydrogenase. More preferably, the oxidoreductase enzyme is at least one of a glucose oxidase, a lactate oxidase, or a haloperoxidase. More preferably, the haloperioxidase enzyme is a chloroperoxidase. Preferably, this dressing of the present invention, as described herein, includes wherein the first polymer may be any number of polymers or co-polymers. The polymers may be for example, but not limited to, cationic, anionic, or nonionic polymers, or combinations thereof. For example, the polymers may be amino methylated poly(acrylamide), quaternized derivatives of N,N-dimethylaminoethylmethacrylate, acrylamide, polyacrylamide, acrylic acid, polyacrylic acid, methacrylic acid, and polysulfostyrene. Preferably, the first polymer is a polyurethane polymer or a polyethylene glycol diacrylate polymer. Another embodiment of this dressing, as described herein, includes at least one initiator composition that is disposed on at least the first side of the layer or within the layer, and optionally including wherein the initiator composition is disposed on the second side of the layer or within the layer, wherein the layer is photopolymerized to form a gel or film. Preferably, the initiator composition is an ultraviolet initiator composition. Another embodiment of this dressing, as described herein, further includes at least one inhibitor of catalase activity that is disposed on at least the first side of the layer or within the layer, and optionally including wherein the inhibitor of catalase is disposed on the second side of the layer or within the layer. Preferably, this inhibitor of catalase activity is at least one selected from the group consisting of hydroxylamine, silver, oxy-tetracycline, azide, and dithiothreitol. More preferably, the dressing of the present invention, as described herein, includes wherein this inhibitor of the catalase activity is covalently bonded to the first polymer. In yet another embodiment of this invention, the dressing of the present invention, as described herein, further includes a cover attached to at least a portion of either the first side of the layer or the second side of the layer for adhering the layer to a wound site of a patient or for adhering the layer to an area proximate to the wound site of the patient. More preferably, the dressing of the present invention, as described herein includes wherein the layer is biodegradable.

In another embodiment of this invention, a dressing is provided comprising (i) a single layer comprising a first side and a second side, wherein the first side is facing an opposite direction relative to the second side, and wherein the first side and the second side are disposed in juxtaposition to each other forming the layer having a desired height, length and width; (ii) a first polymer disposed on at least the first side of the layer or within the layer, and optionally including wherein the first polymer is disposed on the second side of the layer or within the layer; (iii) at least one protein that is covalently linked or crosslinked to the first polymer, and wherein the protein is disposed on at least the first side of the layer or within the layer, and optionally including wherein the protein is disposed on the second side of the layer or within the layer; (iv) and an aqueous composition disposed within the layer, wherein the protein is in a sufficient amount to catalyze a conversion of a chemical constituent placed in contact with the layer, and wherein the protein is capable of undergoing hydrolysis in response to a target analyte to release at least one or more of a disinfectant, an antimicrobial, an antioxidant, or combinations thereof from the first polymer. Preferably, for example, the target analyte is a protease. Another embodiment of this dressing, as described herein, further includes at least one biocide composition, wherein the biocide composition is physically entrapped within the first polymer or covalently tethered to the first polymer. In another embodiment of this dressing, as described herein, further includes at least one biocide composition, the biocide composition is physically tethered to the protein or in contact with the crosslinked polymer such that the biocide is released from the crosslinked polymer upon cleavage of the protein from the first polymer. In yet another embodiment of this dressing, as described herein, a cover is attached to at least a portion of either the first side of the layer or the second side of the layer for adhering the layer to a wound site of a patient or for adhering the layer to an area proximate to the wound site of the patient. Preferably, the layer of the dressing is biodegradable.

Another embodiment of this invention provides a method of providing therapy to the dermis or epidermis of a patient comprising placing a dressing in contact with a patient's epidermis or dermis, the dressing comprising (i) a single layer comprising a first side and a second side, wherein the first side is facing an opposite direction relative to the second side, and wherein the first side and the second side are disposed in juxtaposition to each other forming the layer having a desired height, length and width, (ii) a first polymer disposed on at least the first side of the layer or within the layer, and optionally including wherein the first polymer is disposed on the second side of the layer or within the layer, (iii) at least one enzyme contained within the first polymer, and (iv) an aqueous composition contained within the layer, wherein the enzyme is in a sufficient amount to catalyze a conversion of a chemical constituent placed in contact with the layer, and wherein the enzyme is capable of being activated in the presence of a target analyte to release at least one or more of a disinfectant, an antimicrobial, an antioxidant, or combinations thereof from the first polymer; contacting at least one target analyte with the dressing, and preferably the layer of the dressing, for forming at least one product selected from the group of a disinfectant, an antimicrobial, an antioxidant, or combinations thereof; and releasing then product to the patient's epidermis or dermis for providing therapy to the patient. The layer, the first polymer, the enzyme or enzymes, and the aqueous component are as described herein. Preferably, this method includes wherein the enzyme is immobilized within the first polymer or wherein the enzyme is entrapped or embedded within the first polymer. In another embodiment of this invention, the method includes providing at least one inhibitor of catalase activity that is disposed on at least the first side of the layer or within the layer, and optionally including wherein the inhibitor of catalase activity is disposed on the second side of the layer or within the layer. The inhibitor of catalase activity is as described herein.

Another embodiment of the present invention provides a method of providing therapy to the dermis or epidermis of a patient comprising placing a dressing in contact with a patient's epidermis or dermis, the dressing comprising (i) a single layer comprising a first side and a second side, wherein the first side is facing an opposite direction relative to the second side, and wherein the first side and the second side are disposed in juxtaposition to each other forming the layer having a desired height, length and width, (ii) a first polymer disposed on at least the first side of the layer or within the layer, and optionally including wherein the first polymer is disposed on the second side of the layer or within the layer, (iii) at least one protein that is covalently linked or crosslinked to the first polymer, and (iv) an aqueous composition that is disposed within the layer, wherein the protein is in a sufficient amount to catalyze a conversion of a chemical constituent placed in contact with the layer, and wherein the protein is capable of undergoing hydrolysis in response to a target analyte to release at least one or more of a disinfectant, an antimicrobial, an antioxidant, or combinations thereof from the first polymer; contacting at least one target analyte with the dressing for forming at least one product selected from the group of a disinfectant, an antimicrobial, an antioxidant, or combinations thereof; and releasing the product to the patient's epidermis or dermis for providing therapy to the patient. The layer, the first polymer, the protein or proteins, and the aqueous component are as described herein. Preferably, this method includes wherein the protein is immobilized within the first polymer or wherein the protein is entrapped within the first polymer. In another embodiment of this method, the method further includes providing at least one inhibitor of catalase activity that is disposed on at least the first side of the layer or within the layer, and optionally including wherein the inhibitor of catalase is disposed on the second side of the layer or within the layer. Another embodiment of this method includes providing at least one biocide composition, the biocide composition is physically tethered to the protein or in contact with the crosslinked polymer such that the biocide is released from the crosslinked polymer upon cleavage of the protein from the first polymer. The inhibitor of catalase activity and the biocide are as described herein.

Another embodiment of this invention provides a method for inhibiting the growth of a bacteria and/or fungus comprising applying to a surface that is suspect of contamination with bacteria and/or fungus, an effective amount of a material comprising (i) an excipient, (ii) a first polymer mixed with the excipient, (iii) at least one enzyme contained within the first polymer, and (iv) an aqueous composition, wherein the enzyme is in a sufficient amount to catalyze a conversion of a chemical constituent placed in contact with the material, and wherein the enzyme is capable of being activated in the presence of a target analyte to release at least one or more of a disinfectant, an antimicrobial, an antioxidant, or combinations thereof from the first polymer; providing at least one target analyte from the suspect contaminated surface to contact the enzyme for forming at least one product selected from the group consisting of a disinfectant, an antimicrobial, an antioxidant, or combinations thereof; and releasing the product to the surface for inhibiting said bacteria and/or said fungus. The excipient, the first polymer, the enzyme or enzymes, and the aqueous component are as described herein. Preferably, this method includes wherein the enzyme is immobilized within the first polymer or wherein the enzyme is entrapped or embedded within the first polymer. In another embodiment of this invention, the method includes providing at least one inhibitor of catalase activity. The inhibitor of catalase activity is as described herein.

Another embodiment of the present invention includes a method for inhibiting the growth of a bacteria and/or fungus comprising applying to a surface that is suspect of contamination with bacteria and/or fungus, an effective amount of a material comprising (i) an excipient, (ii) a first polymer mixed with the excipient, (iii) at least one protein that is covalently linked or crosslinked to the first polymer, and (iv) an aqueous composition, wherein the protein is in a sufficient amount to catalyze a conversion of a chemical constituent placed in contact with the material, and wherein the protein is capable of undergoing hydrolysis in response to a target analyte to release at least one or more of a disinfectant, an antimicrobial, an antioxidant, or combinations thereof from the first polymer; providing at least one target analyte from the suspect contaminated surface to contact the protein for forming at least one product selected from the group consisting of a disinfectant, an antimicrobial, an antioxidant, or combinations thereof; and releasing the product to the surface for inhibiting the bacteria and/or the fungus. The excipient, the first polymer, the protein or proteins, and the aqueous composition are as described herein. Preferably, this method includes providing wherein the protein is immobilized within the first polymer or wherein the protein is entrapped within the first polymer. In another embodiment of this method, the method further includes applying at least one inhibitor of catalase activity to the surface. In yet another embodiment of this method, the method further includes providing at least one biocide composition, the biocide composition is physically tethered to the protein or in contact with the crosslinked polymer such that the biocide is released from the crosslinked polymer upon cleavage of the protein from the first polymer. The inhibitor of catalase activity and the biocide are as described herein.

EXAMPLES

The following examples show numerous embodiments of the present invention. Based upon the actual performed working examples 2, 3 and 6 of this invention, and the prophetic examples 1, 4, 5, and 7 of this invention, it will be understood that the present invention may use various enzymes. Those persons skilled in the art shall appreciate that the actual performed working examples and the prophetic examples of this invention are not intended to limit the scope of the claims of this invention in any way.

Example 1

Synthesis of a Responsive Hydrogel

In this embodiment of the present invention, a film was selected as the application method of choice, and the formulation was optimized. The final formulation comprises five components: PEG (polyethylene glycol) diacrylate (22 wt %), PEG 10,000 g/mol (33 wt %), a UV (ultraviolet) initiator (10 wt %), a buffer (35 wt %), and modified chloroperoxidase and glucose oxidase enzymes (0.002%). Polyethylene glycol diacrylate (220 mg-molecular weight of 3,400 g/mol) and linear polyethylene glycol (330 mg-10,000 MW) are first added to 50 mM sodium phosphate solution (pH=8.0). Then, 100 µL of 15 wt % 2-hydroxy-1-[4-(2-hydrozyethoxy)phenyl]-2-methyl-1-propanone in ethanol is also added followed by the addition of glucose oxidase (40 units/mL final volume) and chloroperoxidase (20 units/mL final volume). A small volume (100 µL) of the solution was placed between two 25 mm diameter glass cover slips. The sample was then photopolymerized into a gel by exposing it to a 5 W Spectroline UV Lamp (Model UV-4B) for 2 minutes. The resulting polymer film carries biologically active glucose oxidase and chloroperoxidase. It produces chlorine in response to glucose in a sodium chloride salt solution.

Example 2

Synthesis of a Biogenic Amine Responsive Urethane

Figure 8:
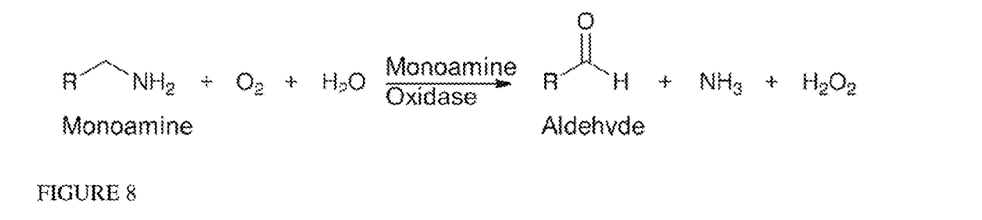
FIG. 8 shows the conversion of a monoamine moiety, oxygen and water to aldehyde, ammonia and hydrogen peroxide in the presence of Monoamine Oxidase (an enzyme).
Figure 9:
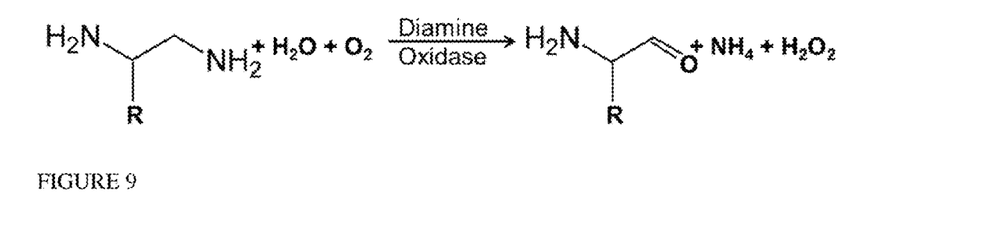
FIG. 9 shows the conversion of a diamine moiety, water and oxygen to a monoamine moiety, ammonium and hydrogen peroxide in the presence of Diamine Oxidase (an enzyme).

A predetermined unit activity of Monoamine Oxidase, Diamine Oxidase, and Peroxidase (1, 75, 108) is mixed together and dissolved in a sufficient amount of Potassium Phosphate Buffer pH 7.5 (50 mM) (See reactions in FIGS. 8 & 9). Unit activity of monoamine oxidase is defined herein as one unit of monoamine oxidase as the amount of enzyme that will oxidize one pmole of tyramine to p-hydroxyphenylacetaldehyde and hydrogen peroxide per minute at pH 7.5 at 37° C. under the specific assay conditions. Unit activity of diamine oxidase is defined as the amount of enzyme that will cause the formation of 1 µmole of hydrogen peroxide from putrescine per minute at pH 8.0 at 30° C. under the specific assay conditions. Unit activity of peroxidase is defined as the amount of enzyme that will form 1.0 mg purpurogallin from pyrogallol in 20 sec at pH 6.0 at 20° C. under the specific assay conditions. The resulting polymer produces chlorine in response to putrescine in a sodium chloride salt solution.

The enzyme solution polymerized is described in U.S. Pat. No. 6,759,220, the content thereof is incorporated by reference herein. For example, the enzyme solution was polymerized as follows. In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases. As used herein, the term "surfactant: refers generally to a surface active agent that is reduces the surface tension of a liquid (water, for example) in which it is dissolved. Preferably, the surfactant is nonionic and comprises between 0.5 to 5.0 weight percent of the aqueous component of the mixture. In the synthesis of the polyurethanes of the present invention, urethane prepolymers were mixed with water. The aqueous component of the reaction mixture included water, enzyme, surfactant and buffer salts. The weight percent surfactant in the aqueous component is thus calculated by dividing the weight of the surfactant by the weight of the entire aqueous component and multiplying the result by 100%. The enzyme loading in the present invention can be greater than approximately 0.1 percent by weight of the polyurethane polymer (weight of enzyme/ [weight of enzyme-containing polymer product]*100%) while retaining substantial enzyme activity. Relatively high activity is maintained even when the enzyme loading is greater that approximately 0.5 percent by weight of the polyurethane polymer. Indeed, relatively high activity is maintained even when the enzyme loading is greater that approximately 1 percent by weight of the polyurethane polymer. The polyurethane polymers of the present invention preferably include at least one of an oxidoreductase, a transferase, a hydrolase, a lyase, an isomerase or a ligase. Examples of enzymes suitable for use in the present invention include, but are not limited to, a lipase, a peroxidase, a tyrosinase, a glycosidase, a nuclease, a aldolase, a phosphatase, a sulfatase, or a dehydrogenase. It will be understood that in a preferred embodiment of the present invention more than one type of enzyme are easily co-immobilized within the polyurethane polymer. The enzymes can be within the same class (for example, two hydrolases) or a within different classes of enzyme. In another aspect, the present invention provides a polyurethane polymer containing an enzyme loading of more than approximately 0.1 weight percent. The polyurethane polymer is synthesized in the presence of a sufficient amount of a surfactant (preferably, nonionic) to increase enzyme activity at the enzyme loading of the polymer (as compared to the case when no surfactant is used). In still another aspect, the present invention provides a method of improving enzymatic activity of a polyurethane polymer synthesized with an enzyme loading of more than approximately 0.1 weight percent. The method includes the step of: adding a sufficient amount of a surfactant (preferably, nonionic) to during synthesis of the polyurethane polymer to increase enzyme activity at the enzyme loading. The polymers and methods of the present invention provide enhanced enzyme activity retention as the enzyme loading or enzyme content of such polymers is increased (for example, to above approximately 0.1 weight percent of the polymer). Relatively large quantities of enzymes are immobilized within the polymers of the present invention while retaining a significant portion of the native enzyme specific activity.

The enzyme-containing polyurethane polymers of the present invention can, for example, be synthesized by reaction of relatively hydrophilic polyurethane prepolymer with aqueous solution to produce a urethane foam. The polyurethane prepolymers used in the present studies were urethanes that were capped (that is, functionalized at chain ends) with multiple isocyanate functionalities. Prepolymers containing multiple isocyanate functionalities have the ability to form chemical crosslinks upon reaction with a diol or water. Water reacts with isocyanates, initiating a foaming reaction in which a carbamic acid intermediate is formed. The carbamic acid quickly degrades to an amine and evolves $CO_2$. The carbon dioxide bubbles through the highly viscous reacting polymer solution, creating a porous foam structure. Because amines readily react with isocyanates, a multi-functional prepolymer in aqueous solution results in a crosslinked polyurethane matrix. Because the vast majority of enzymes are most active in aqueous solution, water not only serves to initiate the prepolymeric reaction, but also provides a route to deliver an enzyme to the reaction. Proteins such as enzymes have many amine groups present via lysine residues and can readily react with isocyanate functionalities to form a crosslinked polymer-protein network through multi-point attachments of the enzyme and polymer. A prepolymer molecule (for example, having a molecular weight of approximately 300 to approximately 10,000) may have multiple isocyanate functionalities/groups. Further, an enzyme may have a reactive amine functionality present via lysine residues and at the N-terminus of the protein.

It is believed that the surfactants used in synthesis of enzyme-containing polyurethane polymers of the present invention enhance the activity of biocatalytic polymers when the enzymatic content of the composite materials is sufficiently high to overwhelm the capacity of the polymer to provide the enzyme incorporated therein with sufficient access to bind substrate or to release product at a rate equivalent to the maximum achievable catalytic rate. In that regard, polymers with excessive enzyme content are diffusionally limited in their ability to catalyze reactions. It is believed, that the use of certain surfactants over a range of concentrations eliminates the diffusional limitations imposed by a polymeric superstructure within which relatively large amounts of enzyme have been incorporated. As known in the art, variation of reaction conditions affects both the physical properties polyurethane foams and the degree of enzyme-foam interaction. Described below is a typical procedure for biopolymer synthesis used in the present invention. Initially, 4 ml of pH 7.8 Tris buffer (10 mm) containing a specific surfactant at a particular concentration (approximately 0 to 8 weight percent in the studies of the present invention) were placed into a narrow cylindrical mixing vessel. Subsequently, an enzyme solution (for example approximately 1 ml of 1.5 mg/ml urease in the same buffer, for example) was added. Finally, approximately 4 ml of Hypol prepolymer, available from Hampshire Chemical Corp., a subsidiary of Dow Chemical Company, (preheated to 30° C. to limit handling problems resulting from high viscosity) were added to the mixture. The solutions was then intimately mixed. During the initial "cream" period, the solution was injected into a cylindrical mold where it rose and then set within 2 to 5 minutes. Polymer synthesis was complete in less than 10 minutes. The $CO_2$ evolved during the reaction of water and isocyanate lifted, the foam to a final volume of approximately 50 to 60 ml. After the initial 10 minute "set-up" time, foam samples were treated in several ways. Some foam samples were immediately sealed in vials, while others were pre-rinsed. Bulk foam samples were typically placed in a fume hood or lyophilizer to facilitate the removal of residual water and $CO_2$ still present from the reaction. Foams were stored under a wide range of conditions until being assayed for enzyme activity. The mixing system used in the present studies required 30 to 40 seconds of mixing at 2500 rpm to create a high quality foam with Hypol 3000, a toluene di-isocyanate based prepolymer. The mixing system included an oar-shaped metal loop having a height of 3.2 cm and a diameter of 1.3 cm. Hypol 5000 (methylene bis(p-phenyl isocyanate) based), a more hydrophobic prepolymer, required additional mixing. Insufficient mixing can result in un-reacted residual prepolymer dispersed within a dense hard mass of polyurethane. Overmixing does not allow the evolving $CO_2$ to act in lifting the foam. Properly mixed foam will typically increase approximately six-fold in volume throughout the course of the reaction.

In one embodiment of the present invention, an aqueous solution of enzymes and surfactant was contacted with an isocyanate-based prepolymer under sufficient agitation to initiate reaction. The enzyme can, for example, be added as a freeze-dried powder or aqueous solution that is either pure or impure. The term "impure" a used herein refers generally to enzymes containing, for example, other proteins/enzymes and biological molecules. Virtually any enzyme or combination of enzymes can be co-immobilized within the same polymer in the present invention.

In model studies of the present invention, enzyme-containing polymers were synthesized both with and without a series of surfactants. Enzymes incorporated into the polymers of the present invention included, for example, organophosphorus hydrolase (OPH), organophosphorus acid anhydrolase (OPAA), butyrylcholinesterase (BChE), urease, and subtilisin carlsberg.

Example 3

Chlorination Response of Tailored Biopolymer to Glucose

The chlorinating activity of composite polymers was measured by following the chlorination of a colored substrate (thionin). The thionin is a blue-violet dye that absorbs at 598 nm and undergoes bleaching (to colorless) upon chlorination. A battery of tests were carried out in 100 mM phosphate citrate buffer at pH 4.0. The reactions employed the following reagents: 0.025 mM thionin and 20 mM NaCl (in citrate phosphate buffer), 0.3% v/v hydrogen peroxide (in deionized water), 18% w/v β-D-glucose (in deionized water), 20 Units/mL of chloroperoxidase in citrate phosphate buffer (where one unit of chloroperoxidase will catalyze the conversion of 1 umole monochlorodimedon to dichlorodimedone per minute at pH 2.75 and 25° C.) and 40 Units/mL of glucose oxidase (where one unit of glucose oxidase will oxidize 1.0 μ mole of β-D-glucose to D-gluconolactone and hydrogen peroxide per minute at pH 5.1 at 35° C.). The reaction mixture comprised 1.45 mL of the thionin/NaCl solution, 30 μL of the substrate solution (glucose or peroxide), and 25 μL of the enzyme solution (total). Buffer was used to replace the enzyme or substrate in control reactions. The absorbance of the thionin/NaCl solution at 598 nm was 0.668 and did not change over two minutes. A reaction mixture containing the thionin/NaCl solution and peroxide had an absorbance of 0.670 over a period of two minutes. A control reaction was carried out to demonstrate the color disappearance of the thionin when chloroperoxidase reacts with the hydrogen peroxide solution and NaCl. The absorbance of the thionin decreased from 0.667 to 0.377 over the course of two minutes, indicating the chlorination of the thionin was occurring. When glucose oxidase and glucose were added to the thionin/NaCl solution, no color change was observed as the absorbance remained constant at 0.670 over two minutes. When the chloroperoxidase was added to glucose in the thionin/NaCl solution without glucose oxidase present, no color change occurred. A color change did occur when chloroperoxidase was added to a solution containing glucose oxidase, glucose, and the thionin/NaCl solution. An absorbance change from 0.680 to 0.456 over two minutes indicated that the enzymatically-generated hydrogen peroxide and NaCl were being used by chloroperoxidase to chlorinate thionin.

Further, an enzyme-containing polyurethane polymer was used to test the chlorination of thionin in the presence of glucose and sodium chloride. A 50 mg polymer containing approximately 9.5 units/g (units/gram) chloroperoxidase and 80 units/g glucose oxidase was added to a 1.925 mL of citrate phosphate buffer and NaCl (20 mM). A 75 µL aliquot of the glucose solution was added to the stirred reactor. The solution was stirred for five minutes, at which point a 725 µL aliquot was taken and added to 725 µL of a 0.025 mM thionin solution in citrate phosphate buffer. The absorbance decreased from 0.301 to 0.212 over a period of 2 minutes. The same experiment was performed using a 50 mg polymer that did not contain enzyme. The absorbance remained constant for two minutes.

Example 4

Synthesis of a Protease-Triggered Erodible Hydrogel

One gram of bovine serum albumin, and 10 mg of fluorescent dextran were dissolved to 20 mL Tris buffer (50 mM, pH 7). Two grams of a toluene diisocyanate based prepolymer (Dow Chemical; trade name HYPOL 2060) is immediately added under mechanical mixing for less than about one minute. The prepolymer is a partially polymerized product of 2,4-toluene diisocyanate and 2,6-toluene diisocyanate with a polyethylene and polypropylene oxides, in which the resulting prepolymer has multiple terminal isocyanate groups. The resulting protein-polymer gel had a mass of about 20 g.

Example 5

Erosion of the Biopolymer from Example 4

Polymer samples were cut from the bulk polymer described in Example 4 above and weighed. The samples were then stored (duplicates) in 3 different environments for 24 hours. 30 mL of Tris buffer (50 mM) pH 8.0 supplemented with 0.05 wt % sodium azide (antibacterial agent) was used as a control solution. Azide was added as a means to straightforwardly prevent microbial contamination during the experiment. The two other incubating solutions contained trypsin at varying levels, 0.1 and 0.8 mg/mL respectively. After 24 hours of incubation, roughly 20% of the dextran within the polymer section diffused out of the gel and was detected in the bulk solution. Proteolytic activity of the surrounding solutions caused the albumin component of the gels to hydrolyze, effectively increasing the distance between molecular crosslinks. As such, 55% and 80% of the entrained dextran was released from the polymers when incubated in 0.1 and 0.8 mg/mL trypsin, respectively.

Example 6

Utilization of Microbial Metabolites to Inhibit Microbial Growth

The microorganism, *Staphylococcus aureus* (*S. aureus*/Staph), was utilized. *Staphylococcus aureus* is an important bacterium to study and ultimately have the ability to inhibit, as *Staphylococcus* can cause a number of diseases as a result of infection. The strain Methicillin-resistant *Staphylococcus aureus* or MRSA is a multi-drug resistant bacterium, making any MRSA infection difficult to treat with standard antibiotics and is thus a more dangerous infection; the number of drug-resistant MRSA cases has increase by 90% over the past decade. MRSA is the most significant infection encountered in hospital settings, costing US hospitals $3.2 to 4.2 billion annually to treat infected patients. Patients with MRSA infections often require longer hospital stays and more time spent in intensive care units. The present invention utilizes a metabolite *S. aureus* produces, namely lactic acid, and converts it to hydrogen peroxide using the enzyme Lactate oxidase (LOx).

Figure 1:
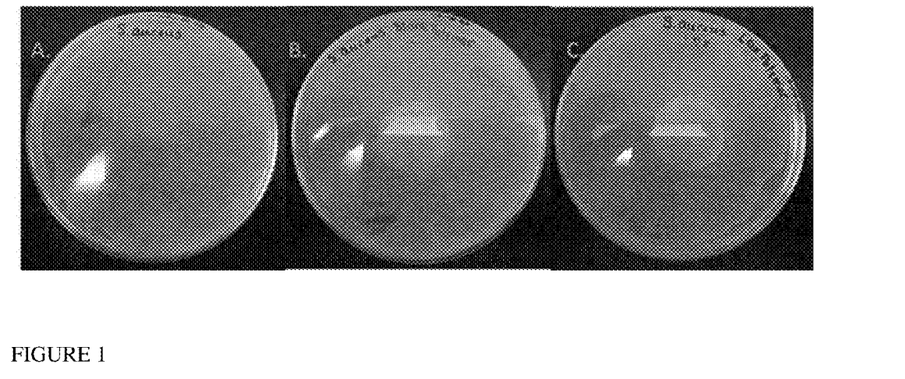
FIG. 1 shows *S. aureus* growth after 18 hours of incubation at 37 C, on TSA plates that contain no catalase inhibitor, Hydroxylamine (HA). A) *S. aureus* grows well on TSA plates that contain no HA. B) *S. aureus* grows well on TSA plates that contain no HA and a blank polyurethane polymer. C) *S. aureus* grows well on TSA plates that contain no HA and Lactate oxidase polymer.
Figure 2:
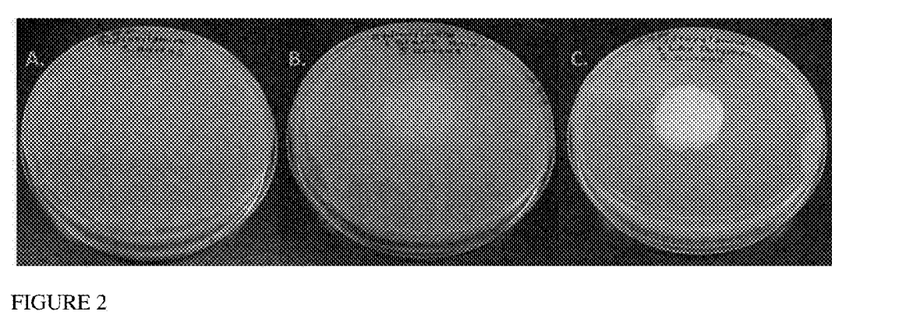
FIG. 2 shows *S. aureus* growth after 18 hours of incubation at 37 C, on TSA plates containing 500 uM of Hydroxylamine, a catalase inhibitor. A) The growth of *S. aureus* is not effected by the presence of Hydroxylamine (HA). B) *S. aureus* growth is normal in the presence of both a non-enzyme containing polymer and the presence of HA. C) HA inhibits catalase activity and therefore it cannot breakdown $H_2O_2$, the $H_2O_2$ produced from LOx's conversion of lactic acid inhibits the growth of *S. aureus* on a solid media.

Lactic acid is produced by *S. aureus* during its normal growth cycle
   The lactate oxidase (LOx) enzyme converts Lactic acid into hydrogen peroxide ($H_2O_2$)
   $H_2O_2$ can inhibit microbial growth
   $H_2O_2$ can further be combined with chloride by the enzyme chloroperoxidase (CPO) to generate reactive oxygen species such as hypochlorous acid (HOCl) and chlorine dioxide ($ClO_2$)
However, the bacteria *S. aureus* is catalase positive.
   Catalase is an enzyme that quickly breaks down $H_2O_2$ into water ($H_2O$) and Oxygen ($O_2$)
   Any hydrogen peroxide produced from the LOx/lactic acid reaction will be converted to water and oxygen by catalase before it can inhibit the growth of *S. aureus*, unless catalase is inhibited
We inhibited catalase with the inhibitor, hydroxylamine (HA), the concentration of HA will have no effect itself on *S. aureus* growth
   Therefore, the $H_2O_2$ produced from the LOx/lactic acid reaction inhibits *S. aureus* growth.
Experimental design: HA at a final concentration of 500 uM was added to trypticase soy agar (TSA—the optimal growth media for *S. aureus*) before pouring plates
   TSA plates (without HA) were also prepared as a control
   After plates were solidified, 100 uL of a 1:10 dilution of *S. aureus* was plated
   *S. aureus* overnight culture was grown from a single colony from a freshly struck plate. This was diluted in sterile water and then plated onto either TSA or TSA+HA plates
   Blank Polymer, 1 U/mg LOx polymer or NO polymer was added to TSA or TSA+HA plates
      250 mg pieces of blank and Lox containing polymer foams were cut and thoroughly rinsed (with sterile dH2O) before adding to the plates
      250 Units=250 mg polymer
   Plates +/− polymer foams were incubated overnight (~18 hours) at 37° C.
Results of the Experiment:
   As shown in FIG. 1, *S. aureus* grows normally with no inhibition on TSA plates that do not contain an inhibitor (FIG. 1A). Polyurethane polymer foams have no enzyme have effect on microbial growth (FIG. 1B). Although LOx polymers convert the lactic acid (which is produced from *S. aureus*) into peroxide, because *S. aureus* is catalase positive and breaks down the hydrogen peroxide that is produced, without a catalase inhibitor present, *S. aureus* growth is not inhibited by LOx polymers (FIG. 1C).
   As shown in FIG. 2, *S. aureus* grows normally with no inhibition on TSA plates that contain the catalase inhibitor, HA. While HA inhibits catalase activity, it does not inhibit the growth of *S. aureus* (FIG. 2A). Non-enzyme containing polyurethane polymer foams have no effect on microbial growth. The composite materials of the polyurethane foam nor does the HA have any effect on *S. aureus* growth (FIG. 2B). HA inhibits catalase activity and therefore it cannot breakdown hydrogen peroxide (which is produced from LOx's conversion of lactic acid). Hydrogen peroxide that is produced from the reaction inhibits the growth of *S. aureus* on a solid media (FIG. 2C).

Those persons skilled in the art understand that the method of the present invention includes wherein the catalase inhibitor is selected from the group consisting of hydroxylamine, silver, silver containing compositions, oxytetracycline, azide, and dithiothreitol.

The method of present invention may be useful in inhibiting other gram positive bacteria, such as for example other *Staphylococcus* bacteria, such as for example but not limited to *Staphylococcus epidermidis*, and for inhibiting gram negative bacteria, such as for example but not limited to *Pseudomonas* bacteria including but not limited to for example *Pseudomonas aeruginosa*, *Klebsiella* bacteria including for example but not limited to *Klebsiella pneumonia*, and *Acinetobacter* bacteria including but not limited to *Acinetobacter baumannii*. The method of the present invention is useful in inhibiting certain fungus growth, such as for example but not limited to fungi belonging to the *Candida* genus, the *Trichophyton* genus, and *Aspergillus* genus. *Trichophyton rubrum* is a fungus that is a common cause of athlete's foot, jock itch, and ringworm infections. *Candida albicans* is a common fungus that causes yeast infections of the mouth, throat, and genitourinary tracts. *Aspergillus niger* is a common fungus contaminant of foods.

In another embodiment of this invention, the method includes applying an effective amount of the LOx enzyme onto a surface suspected of being contaminated with gram positive and/or gram negative bacteria. The treated suspect contaminated surface may thereafter be contacted with an effective amount of HA, or optionally the method includes wherein the LOx enzyme and HA may be simultaneously applied to the suspect contaminated surface. The enzymes may be applied to the contaminated surface by any mechanical means such for example but not limited to brushing, pouring, wiping, and spraying, and combinations thereof. Preferably, the mechanical means includes contacting the contaminated surface with a fabric or a polymer matrix containing one or more enzyme(s). More preferably, the method includes wherein the enzymes are entrapped within or covalently bonded to a polymer matrix. The polymer matrix may be for example, but not limited to a polyurethane foam containing one or more enzyme(s).

In another embodiment of this invention, a method is provided that inhibits the growth of non-catalase positive (i.e catalase negative) bacteria by subjecting the non-catalase positive bacteria and/or fungus to an effective amount of a LOx enzyme to produce an effective amount of hydrogen peroxide which inhibits the microbial growth of the non-catalase positive bacteria or fungus. Non-catalase producing bacteria include for example but are not limited to certain enterobacteriacea. This method optionally further includes subjecting the hydrogen peroxide treated bacteria or fungus with an effective amount of a chloride containing composition, such as for example, by the addition of an effective amount of the enzyme chloroperoxidase (CPO) to generate reactive oxygen species such as hypochlorous acid (HOCl) and chlorine dioxide ($ClO_2$). Preferably, a mechanical means is employed to subject the bacteria and/or fungus with the effective amount of the LOx enzyme, such as for example but not limited to brushing, pouring, wiping, and spraying, and combinations thereof. Preferably, the mechanical means includes contacting the bacteria or fungus with a fabric or a polymer matrix containing one or more enzyme(s). More preferably, the method includes wherein one or more of the enzymes are entrapped within or covalently bonded to a polymer matrix. The polymer matrix may be for example, but not limited to a polyurethane foam containing one or more enzyme(s).

Yet another embodiment of the present invention includes a method of inhibiting the growth of bacteria and/or fungus on a surface contaminated with blood including subjecting the blood contaminated surface with an effective amount of the enzyme lactic oxidase (LOx), followed by subjecting the LOx treated bacteria and/or fungus to an effective amount of chloroperoxidase enzyme, wherein the chloroperoxidase enzyme and the chloride within the blood produce hypochloride and chlorine dioxide. The hypochloride and the chlorine dioxide inhibit catalase producing bacteria. Optionally, the method includes wherein the LOx enzyme and the chloroperoxidase enzyme are simultaneously placed in contact with the blood contaminated surface. The blood may be of either human or animal origin. While not being bound to a particular theory, this embodiment of the invention involves a competitive reaction between the chloroperoxidase enzyme and the chloride present in the blood to form the hypochloride and the chlorine dioxide species. Preferably, a mechanical means is employed to subject the contaminated surface with the effective amount of the LOx enzyme, such as for example but not limited to brushing, pouring, wiping, and spraying, and combinations thereof. Preferably, the mechanical means includes contacting the contaminated surface with a fabric or a polymer matrix containing one or more of the enzyme(s). More preferably, the method includes wherein one or more of the enzymes are entrapped within or covalently bonded to a polymer matrix. The polymer matrix may be for example, but not limited to a polyurethane foam containing one or more enzyme(s).

Figure 6:
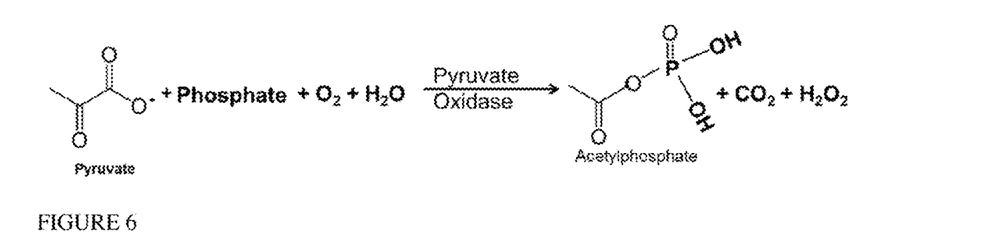
FIG. 6 shows the conversion of pyruvate, phosphate, oxygen and water to acetylphosphate, carbon dioxide and hydrogen peroxide in the presence of Pyruvate Oxidase (an enzyme).
Figure 7:
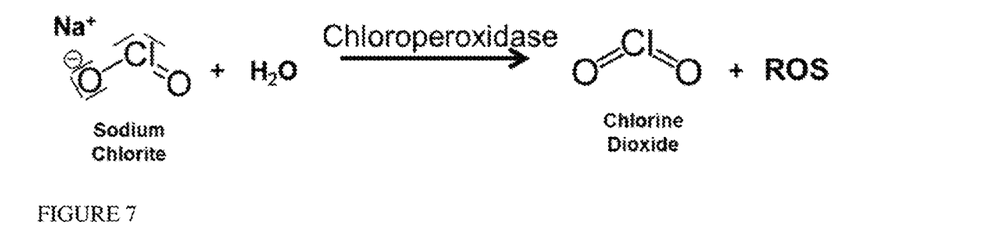
FIG. 7 shows the conversion of sodium chlorite and water to chlorine dioxide and a reactive oxygen species in the presence of Chloroperoxidase (an enzyme).

Another embodiment of the reaction entails the use of two or more oxidase enzymes working in series, with the first enzyme using an environmentally supplied substrate, and each remaining enzyme deriving its substrate from the byproduct of a preceding enzymatic reaction. In this scenario, the amount of hydrogen peroxide produced is amplified by a factor of the number of oxidase enzymes in the series. For example, lactate oxidase catalyzes the conversion of lactic acid into pyruvate and hydrogen peroxide. Coupling lactate oxidase with pyruvate oxidase would double the amount of peroxide produced as the pyruvate oxidase catalyzes the conversion of pyruvate, produced in the first reaction, into acetyl phosphate and hydrogen peroxide (See FIGS. 5 and 6).

As used herein, the term "contaminated surface" or "contaminated surfaces" include(s) for example but is not limited to any surface having a bacteria or fungi, and includes surfaces found in hospitals, including those surfaces found in patient rooms, operating rooms, surfaces of medical equipment and instruments, fabric, natural or manufactured dressings, bed surfaces and rails, and residential and commercial surfaces found in homes and gyms, including shower stalls, and clothing changing areas, and includes surfaces of a patient's body, including but not limited to intact or broken skin of the patient, and wounds of a patient that may be accessible externally or internally of the patient's body.

Example 7

Utilization of Fungal Metabolites to Inhibit Growth on Architecture

A common metabolite, oxalic acid is secreted by fungi to break down the cell wall of plants and trees allowing the fungi to access the proteins inside which eradicates the plants and trees. This microbial metabolite is catalyzed by oxalate oxidase (OXO); OXO is commonly found in fungi resistant plants. In the present embodiment of this invention, a predetermined unit activity of oxalate oxidase will be immobilized or entrapped within a permanent or semi-permanent architectural material, such as for example but not limited to a coating. Oxalate oxidase catalyzes the conversion of oxalate acid to produce carbon dioxide and hydrogen peroxide (a common disinfectant), the enzyme (OXO) will remain passive until fungi is present and will then produce an antimicrobial agent to ward off fungal growth on surfaces. The smart material (or coating) will convert environmentally present chemicals into peroxides or radicals for the inhibition of microbial growth. These materials (or coatings) will be autonomous in that they will not produce disinfectants unless induced by the presence of fungi.

It will be appreciated by those persons skilled in the art that changes could be made to the embodiments described above without departing from the broad inventive concept thereof. These examples are not intended to limit the scope of the present invention as described herein. These examples are for purposes of illustration and it will be evident to those persons skilled in the art that numerous variations and details of the present invention may be made without departing from the present invention as set forth herein. It is understood, therefore, that this invention is not limited to the particular embodiments and examples disclosed, but it is intended to cover modifications that are within the spirit and scope of the invention, as defined in the appended claims.

What is claimed is:

1. A material consisting of:
an excipient;
a polymer mixed with said excipient;
at least one non-catalase enzyme contained within said polymer and wherein said enzyme is non-serum activated, and wherein said enzyme is at least one selected from the group consisting of a transferase, a hydrolase, a lyase, an isomerase, and a ligase;
at least one catalase inhibitor; and
an aqueous composition, wherein said enzyme is in a sufficient amount to catalyze a conversion of a metabolite from a propagating microorganism, said metabolite selected from the group consisting of cadaverine, putrescine, histamine, and tyramine, placed in contact with the material, and wherein said enzyme is capable of being activated in the presence of said metabolite to convert said metabolite into at least one or more of a disinfectant, an antimicrobial, an antioxidant, or combinations thereof from said polymer, wherein said enzyme is passive and converts said metabolite only on demand of a propagating microorganism which expresses and/or secretes said metabolite.

2. The material of claim 1 wherein said enzyme is immobilized within said polymer or entrapped within said polymer.

3. The material of claim 1 wherein said polymer is a polyurethane polymer or a polyethylene glycol diacrylate polymer.

4. The material of claim 1 including at least one initiator composition, and wherein said material is photopolymerized to form a gel or film.

5. The material of claim 1 wherein said antimicrobial includes peroxides and halogen gases.

6. The material of claim 1 wherein said disinfectant is a hydrogen peroxide.

7. The material of claim 1 wherein said inhibitor of catalase activity is at least one selected from the group consisting of hydroxylamine, silver, oxy-tetracycline, azide, and dithiothreitol.

8. The material of claim 1 wherein said inhibitor of said catalase activity is covalently bonded to said polymer.

9. A dressing consisting of:
a single layer comprising a first side and a second side, wherein said first side is facing an opposite direction relative to said second side, and wherein said first side and said second side are disposed in juxtaposition to each other forming said layer having a desired height, length and width;
a polymer disposed on at least said first side of said layer or within said layer, and optionally including wherein said polymer is disposed on said second side of said layer or within said layer;
at least one non-catalase enzyme contained within said polymer and wherein said enzyme is non-serum activated, and wherein said enzyme is at least one selected from the group consisting of a transferase, a hydrolase, a lyase, an isomerase, and a ligase;
at least one inhibitor of catalase activity that is disposed on at least said first side of said layer or within said layer, and optionally including wherein said inhibitor is disposed on said second side of said layer or within said layer; and
an aqueous composition contained within said single layer, wherein said enzyme is in a sufficient amount to catalyze a conversion of a metabolite from a propagating microorganism, said metabolite selected from the group consisting of cadaverine, putrescine, histamine, and tyramine, placed in contact with said layer, and wherein said enzyme is capable of being activated in the presence of said metabolite to convert said metabolite into at least one or more of a disinfectant, an antimicrobial, an antioxidant, or combinations thereof from said polymer, wherein said enzyme is passive and converts said metabolite only on demand of said propagating microorganism which expresses and/or secretes said metabolite.

10. The dressing of claim 9 wherein said layer is a film, a fiber, a fabric, a thread, a gauze, or a polymeric composition.

11. The dressing of claim 9 wherein said enzyme is immobilized within said polymer or wherein said enzyme is entrapped within said polymer.

12. The dressing of claim 9 wherein said polymer is a polyurethane polymer or a polyethylene glycol diacrylate polymer.

13. The dressing of claim 9 including at least one initiator composition that is disposed on at least said first side of said layer or within said layer, and optionally including wherein said initiator composition is disposed on said second side of said layer or within said layer, wherein said layer is photopolymerized to form a gel or film.

14. The dressing of claim 9 wherein said antimicrobial includes peroxides and halogen gases.

15. The dressing of claim 9 wherein said disinfectant is a hydrogen peroxide.

16. The dressing of claim 9 wherein said inhibitor of catalase activity is at least one selected from the group consisting of hydroxylamine, silver, oxy-tetracycline, azide, and dithiothreitol.

17. The dressing of claim 9 wherein said inhibitor of said catalase activity is covalently bonded to said polymer.

18. The dressing of claim 9 including a cover attached to at least a portion of either said first side of said layer or said second side of said layer for adhering the layer to a wound site of a patient or for adhering the layer to an area proximate to said wound site of said patient.

19. The dressing of claim 9 wherein said layer is biodegradable.

\* \* \* \* \*